(12) United States Patent
Parker

(10) Patent No.: US 7,431,882 B2
(45) Date of Patent: Oct. 7, 2008

(54) DRUG TEST KIT

(75) Inventor: James E. Parker, Pomona, CA (US)

(73) Assignee: Modern Optics, Inc., Pomona, CA (US)

( * ) Notice: Subject to any disclaimer, the term of this patent is extended or adjusted under 35 U.S.C. 154(b) by 614 days.

(21) Appl. No.: 09/752,712

(22) Filed: Dec. 28, 2000

(65) Prior Publication Data

US 2002/0085953 A1    Jul. 4, 2002

(51) Int. Cl.
*G01N 33/00*    (2006.01)
(52) U.S. Cl. .............................. 422/61; 422/55; 422/56; 422/58; 422/100; 422/102
(58) Field of Classification Search .................. 422/55, 422/58, 61, 68.1, 102, 56, 57, 100; 436/165, 436/178
See application file for complete search history.

(56) References Cited

U.S. PATENT DOCUMENTS

| | | | | |
|---|---|---|---|---|
| 3,849,256 A | * | 11/1974 | Linder | ...................... 435/287.7 |
| 5,119,830 A | | 6/1992 | Davis | |
| 5,403,551 A | | 4/1995 | Galloway et al. | |
| 5,916,815 A | | 6/1999 | Lappe | |
| 5,976,895 A | * | 11/1999 | Cipkowski | ................... 436/518 |
| 6,168,758 B1 | * | 1/2001 | Forsberg et al. | ................ 422/61 |
| 6,342,183 B1 | | 1/2002 | Lappe et al. | |
| 6,372,515 B1 | | 4/2002 | Casterlin et al. | |
| 6,379,620 B1 | * | 4/2002 | Tydings et al. | ................. 422/58 |
| 6,627,152 B1 | * | 9/2003 | Wong | .......................... 422/58 |

FOREIGN PATENT DOCUMENTS

WO    WO 00/29111    *    5/2000

* cited by examiner

*Primary Examiner*—Sam P Siefke
(74) *Attorney, Agent, or Firm*—Fulwider Patton LLP

(57) ABSTRACT

The assaying apparatus provides a kit in a collection cup for collecting and analyzing a urine sample for drugs or drug metabolites. In one embodiment, a separator member is disposed in the interior of the cup, separating an isolated liquid sample space from the assay regions of the assay strips. Wicking of the urine sample provides a controlled flow to the assay regions of the assay strips. The cup includes a pair of ribs on the interior surface of the cup forming a slot for receiving and retaining the assay strips and the wick assembly. In a second embodiment, collection cup has a cap with assay strips, and a wick mounted to the cap and extending into the liquid sample space of the collection cup when the cap is placed on the cup, for wicking the liquid sample from the interior of the cup to the assay strips. A transparent cover is provided over the assay strips permitting observation of the results of the assays.

6 Claims, 4 Drawing Sheets

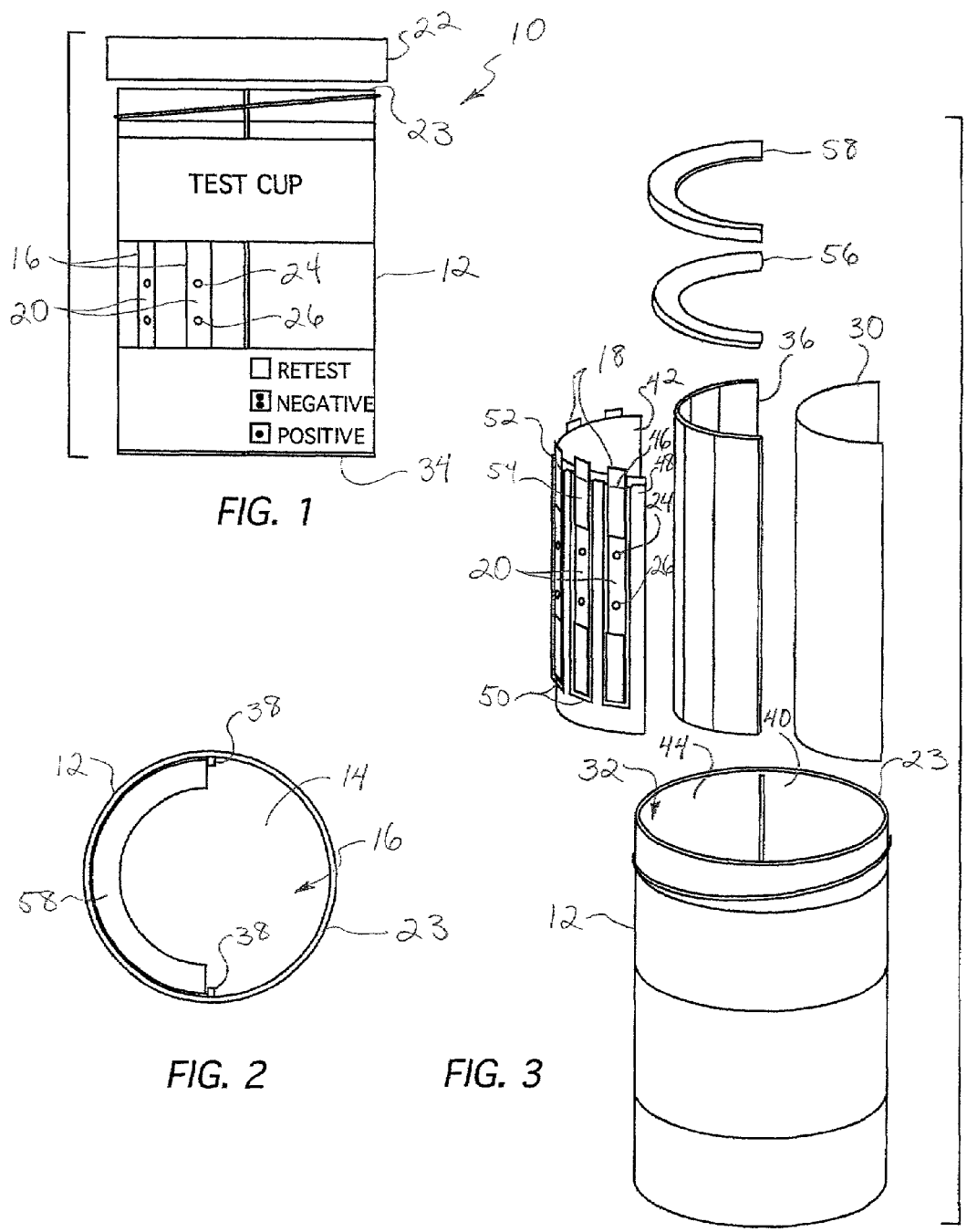

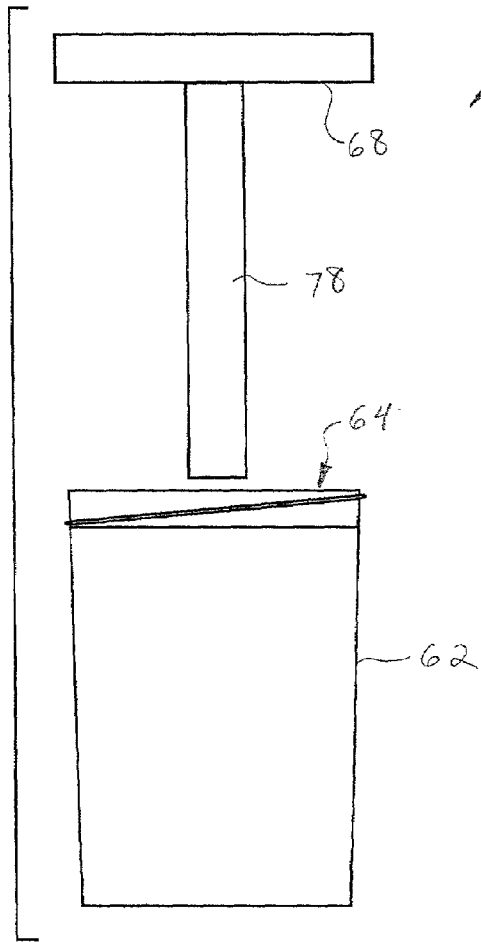
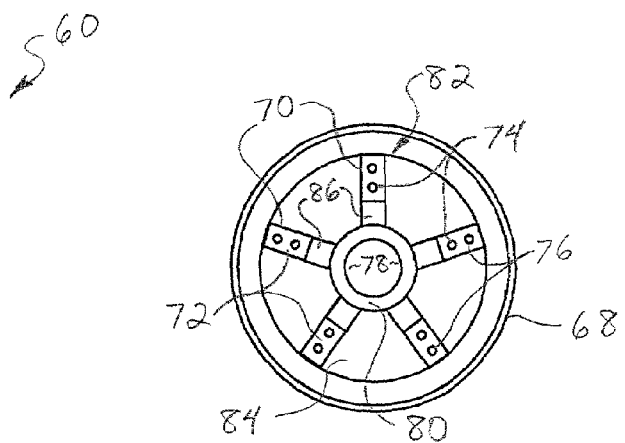
FIG. 5
FIG. 4

DRUG TEST KIT

BACKGROUND OF THE INVENTION

1. Field of the Invention

This invention relates generally to assaying devices, and more particularly concerns collection cup devices for determining the presence of a plurality of chemical analytes in a liquid sample.

2. Description of Related Art

Drugs such as amphetamines, cocaine, morphine, PCP or marijuana are typically administered by injection, orally, intranasal insufflation or inhalation. Such drugs are rapidly metabolized in the body and converted to a number of drug metabolites that are excreted in the urine. Drug screening assays are therefore typically based upon the detection of such urinary drug metabolites. Methods for drug testing have evolved from such laborious procedures as thin layer chromatography and liquid chromatography to a variety of immunological procedures such as radioimmunoassay, enzyme immunoassay, and immunochromatographical assays. The immunochromatographical techniques have simplified drug testing procedures so that multiple drug test screens can be performed simultaneously, without expensive, complicated instrumentation.

One known assaying device for both collecting and analyzing a sample includes a container and an opening for collecting the sample in a chamber for storing the sample. A cap is provided for sealing the container opening and at least one assay system is attached to the container for chemically analyzing the sample. A channel is provided for a portion of the sample to enter the assay system upon a change of orientation of the container. However, in order to carry out drug testing, once the specimen is introduced into the test container, the test container must be closed and sealed, and then gently tilted toward the front label until the specimen covers approximately ½ to ¾ of the cap, without inverting the container, for ten seconds, and then the container must be returned to an upright position.

Another known diagnostic testing device includes a base and a cover which defines an opening for receiving a liquid specimen. A distribution wheel delivers portions of the specimen to circumferentially spaced antibiotic units. A delivery cylinder extends upwardly from each of the antibiotic units toward corresponding indicator units in communication with the cover member. However, relative vertical movement between the delivery cylinder and the indicator units is required to place the cylinder and the indicator units into an engaging relationship.

In another known binding assaying apparatus, a controlled flow of a specific binding reagent is introduced through a top absorbent membrane in parallel contact with a main absorbent membrane. A parallel flow of liquid occurs in the two membranes, and the controlled flow of the diluted reagent from the top absorbent membrane into the main absorbent membrane results in a uniform dilution of the reagent.

A need therefore continues to exist for an assaying apparatus for collecting and analyzing a liquid sample, such as urine, for the presence or absence of a plurality of analytes such as drug metabolites in the liquid sample, that does not require any special handling or pretreatment procedures, so that the testing can be carried out simply and with a minimization of assaying errors due to improper handling of the specimens once they are introduced into the container. The present invention meets these needs.

SUMMARY OF THE INVENTION

Briefly, and in general terms, the present invention provides for an assaying apparatus for collecting and analyzing a liquid sample, such as urine, for the presence or absence of a plurality of analytes such as drug metabolites in the liquid sample, that provides for automatic wicking of the liquid sample to an assay region of an assay strip isolated within an assay container once the liquid sample is introduced into the assaying container, providing a controlled flow of the liquid sample to the assay region of the assay strip.

The present invention accordingly provides for an assaying apparatus for collecting and analyzing a liquid sample for the presence or absence of a plurality of analytes in the liquid sample. In a first preferred embodiment of the invention, the apparatus comprising a sealable container for receiving a liquid sample in an interior chamber with a liquid sample space, with one or more assay strips disposed in the interior chamber of the container, and each of the assay strips having an assay region for indicating the presence or absence of an analyte in a liquid sample placed in the liquid sample space of the interior chamber of the container. A separator member is disposed in the interior chamber separating the liquid sample space from the assay regions of the assay strips, and wick means are disposed in the interior chamber of the container in fluid communication with the assay strip for conducting a portion of the liquid sample from the interior chamber of the container to the assay regions of the assay strips.

In a presently preferred aspect of the first embodiment of the invention, the container includes a pair of ribs on the interior surface of the interior chamber of the container forming a slot for receiving and retaining the assay strips and wick. In another preferred aspect, each of the assay strips includes wicking material for conducting the liquid sample from the wick to the assay region of the assay strip. A bridging wick piece can be provided adjacent to and in fluid communication with the wick means and in immediate contact with the assay strips for conducting the liquid sample from the wick to the assay strips, and a retainer member can be disposed over the assay strips, bridging wick piece and wick means for retaining the assay strip, bridging wick piece and wick means in place in the interior chamber of the container.

In a second preferred embodiment of the invention the assaying apparatus for collecting and analyzing a liquid sample for the presence or absence of a plurality of analytes in the liquid sample comprises a container having an interior sample chamber with a liquid sample space for receiving a liquid sample, and a cap adapted to be placed over the container opening for closing the container opening and sealing the container. One or more assay strips are disposed in the cap, with each assay strip having an assay region for indicating the presence or absence of one of a plurality of analytes in a liquid sample placed in the liquid sample space of the interior chamber of the container, and a wick mounted to the cap and extending into the liquid sample space of the interior sample chamber when the cap is placed on the container. The wick is in fluid communication with the assay strip for conducting a portion of the liquid sample from the interior chamber of the container to the assay region of the assay strip. In a presently preferred aspect of the second embodiment, a transparent cover is provided over the assay strips permitting observation of the results of the assays. The cap advantageously can have a separator member disposed between the assay strips and the interior chamber of the container for separating the liquid sample space from the assay region of the assay strip, and the assay strips can also include wicking material for conducting the liquid sample from the wick to the assay regions of the assay strips. In one presently preferred aspect of the second embodiment, a bridging wick piece is provided adjacent to and in fluid communication with the wick and in immediate contact with the assay strips for conducting the liquid sample from the wick to the assay strips.

In further preferred embodiments, the invention provides for an assaying apparatus for collecting and analyzing a liquid sample for the presence or absence of at least one analyte in the liquid sample, with the apparatus comprising means for receiving a liquid sample, and a test strip holder. The test strip holder includes at least one assay strip, and each assay strip has an assay region for indicating the presence or absence of an analyte in a liquid sample placed in the liquid sample space of the interior chamber of the container. In one presently preferred embodiment, the means for receiving a liquid sample comprises a tube, and in another presently preferred embodiment, the means for receiving a liquid sample comprises a collection vial, which may also serve as a protective mailing tube for transporting the sample. The collection vial preferably includes means for engaging the test strip holder. Wicking material may be provided in each test strip for conducting the liquid sample from the means for receiving a liquid sample to the assay region of the assay strip. A wick may also be mounted to the test strip holder and adapted to extend between the means for receiving a liquid sample and each of the assay strips.

These and other aspects and advantages of the invention will become apparent from the following detailed description and the accompanying drawings, which illustrate by way of example the features of the invention.

BRIEF DESCRIPTION OF THE DRAWINGS

FIG. 1 is a side elevational view of a first embodiment of the drug test kit according to the principles of the invention;

FIG. 2 is a top plan view of the drug test kit of FIG. 1;

FIG. 3 is an exploded perspective view of the drug test kit of FIG. 1;

FIG. 4 is an exploded side view of a second embodiment of the drug test kit according to the principles of the invention;

FIG. 5 is a top plan view of the drug test kit of FIG. 4;

DETAILED DESCRIPTION OF THE PREFERRED EMBODIMENTS

Figure 6:
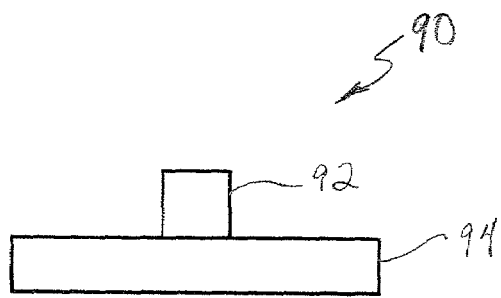
FIG. 6 is a side view of a third embodiment of the drug test kit according to the principles of the invention.

While immunochromatographical techniques have now been developed for multiple drug test screens that can be performed simultaneously, the various types of conventional collection cup devices available typically require careful and special handling for the drug testing to be effective, so that errors in the testing procedure can be introduced due to improper handling of the specimens once they are introduced into the container.

As is illustrated in the drawings, the invention is accordingly embodied in an assaying apparatus for collecting and analyzing a liquid sample, such as urine, for the presence or absence of a plurality of analytes such as drug metabolites in the liquid sample, that provides for automatic wicking of the liquid sample to an assay region of an assay strip isolated within an assay container once the liquid sample is introduced into the assaying container, providing a controlled flow of the liquid sample to the assay region of the assay strip, and that does not require any special handling or pretreatment procedures.

In a first preferred embodiment illustrated in FIGS. 1-3, an assaying apparatus 10 is provided for collecting and analyzing a liquid sample for the presence or absence of a plurality of analytes in the liquid sample. The assaying apparatus comprises a sealable container such as a transparent collection cup 12, for receiving a liquid sample, such as a urine sample, for example, in a liquid sample space 14 provided in the interior chamber 16 of the container. One or more assay strips 18 are provided in the interior chamber of the container, with each of the assay strips have an assay region 20 for indicating the presence or absence of an analyte in a liquid sample placed in the liquid sample space of the interior chamber of the container. A cap 22 is provided to be placed on and seal the mount 23 of the container.

The assay strips preferably utilize a competitive binding inhibition assay. The drug or drug metabolite-conjugate is bound to a portion of a membrane on the assay strips in the form of a dot 24 affixed to the membrane. When the liquid sample, such as urine, for example, is collected in the container, the urine flows along the membrane by capillary action, and mixes with an antibody-coated red particle formed from a colloidal sensing mixture dried on the membrane. If the particular drug or drug metabolite to which the antibody is sensitive is present in the urine, the drug or drug metabolite will react with the antibody-coated red particle and prevent it from reacting with a drug-conjugate on the membrane, and no red dot will be visible, indicating a Positive test result. If none of the drug or drug metabolite is present in the urine, the antibody-coated red particle will react with the drug-conjugate on the membrane to form a visibly red dot, indicating a Negative test result. Another reactive area is provided as a procedural control dot 26, under the test area, containing fixed immunoglobulin on the membrane. This antibody in the control dot is an antisera to the antibody coating the red particle, which is captured and forms a red dot, as an indication that the test is valid. If the area does not form a red dot for all tests, the test is considered invalid, and needs to be repeated.

In a presently preferred embodiment, each container is provided with five partitioned membrane test strips. Each strip tests for a specific drug or drug metabolite. The test strips typically contain one of the following:

1. Colloidal gold coated with sheep polyclonal anti-amphetamine, mouse monoclonal anti-benzoylecgonine, polyclonal rabbit anti-morphine-3 glucuronide, mouse monoclonal anti-cannabinoid or mouse monoclonal anti-phencyclidine;
2. The appropriate drug or drug analog conjugates immobilized on the membrane; and
3. Immobilized antisera to the gamma globulin to the animal producing the anti-drug sera (on the procedural control dot).

As is illustrated in FIG. 3, a planar separator member 30 typically formed of plastic such as polystyrene, Mylar backed sheets, or plastic laminated paper, is disposed in the interior chamber generally separating the interior chamber into the liquid sample space and an assay space 32 for the assay strips. The separator member does not, however, extend all the way to the bottom 34 of the container, leaving a small space for the liquid sample to flow underneath the separator member from the liquid sample space to the assay space. A main wick 36, including one or more wicks typically formed of fabric wicking material such as cotton or other suitable natural or synthetic fabric, is disposed in the assay space of the container for absorbing the liquid sample admitted to the assay space underneath the separator member. The wicks extend upward to be in fluid communication with the assay strips for conducting a portion of the liquid sample from the interior chamber of the container to the assay strips. The separator member and the main wick can be inserted and held in place in the collection cup by a pair of ribs 38 on the interior surface 40 of the interior chamber of the cup, forming a slot for receiving and retaining the wick and the assay strips, as will be further explained below.

The assay strips are preferably mounted on a flexible plastic or plastic laminated paper backing 42 that can also be inserted between the wall 44 of the container and the wick assembly, and is held in place in the container in the slot formed by the pair of ribs on the interior surface of the interior chamber of the cup. Each of the assay strips are inserted in slots 46 formed on the backing 42, such as by a clear plastic laminate 48 bonded to the backing 42, with each of the slots being closed and sealed at the bottom 50 and open at the top 52, allowing the liquid sample to be communicated to the assay strips only from the top. Each of the assay strips preferably includes a thin layer of wicking material 54 for conducting the liquid sample from the wick to the assay region of the assay strip, to provide a gradual, uniform flow of the liquid sample to the assay strips, although the liquid sample could also simply drip from the wick assembly down the backing of the assay strips. A bridging wick piece 56 can also be provided between the main wick and the assay strips, in immediate contact with the assay strips for conducting the liquid sample from the main wick to the assay strips. A retainer member 58 is also preferably placed over the assay strips, the bridging wick piece and the main wick, and held in place in the cup between the ribs on the interior surface of the cup, for retaining the assay strip, bridging wick piece and the main wick in place in the interior chamber of the container.

In a second preferred embodiment, illustrated in FIGS. 4 and 5, the assaying apparatus 60 comprises a container 62, such as a collection cup, having an interior sample chamber 64 providing a liquid sample space for receiving a liquid sample, and a cap 68 adapted to be placed over the container opening for closing the container opening and sealing the container. One or more assay strips 70 as described above are preferably disposed in the cap, with each assay strip having an assay region 72 with a test dot 74 and a control dot 76 for indicating the presence or absence of one of a plurality of analytes in a liquid sample placed in the liquid sample space of the interior chamber of the container. As in the first embodiment, five assay strips are preferably provided, as is shown in FIG. 5.

A main wick 78, typically formed of a fibrous material that can be natural or synthetic, such as cotton, for example, is mounted to the cap, such as by adhesive, and extends into the interior sample chamber when the cap is placed on the container. The main wick is preferably connected to the assay strips by an annular bridging wick material 80, typically formed of fabric wicking material such as cotton or other suitable natural or synthetic fabric, for conducting a portion of the liquid sample from the interior chamber of the container to the assay region of the assay strip. A transparent cover 82, such as a piece of transparent plastic, for example, is provided on the cap over the assay strips permitting observation of the results of the assays. A separator member 84, typically formed of plastic such as polystyrene, Mylar backed sheets, or plastic laminated paper, is disposed between the assay strips and the interior chamber of the container for separating the liquid sample space from the assay strips. The assay strips can also include wicking material 86 for conducting the liquid sample from the wick to the assay regions of the assay strips.

Figure 7:
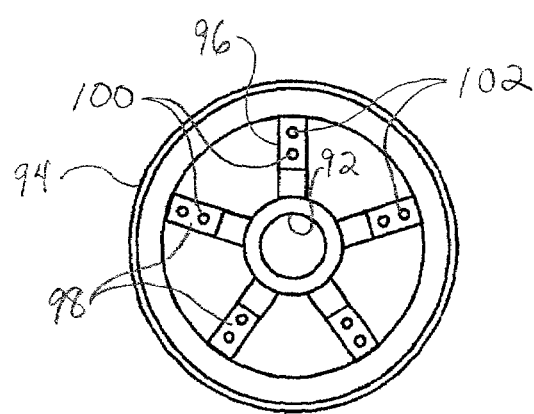
FIG. 7 is a top plan view of the drug test kit of FIG. 6.

In a third preferred embodiment, illustrated in FIGS. 6 and 7, the assaying apparatus 90 comprises a sample tube 92 for receiving a liquid sample, and a test strip holder 94 centrally connected to the adapted to the sample tube, with the interior of the sample tube in communication with the inner ends of one or more assay strips 96 as described above, disposed in the test strip holder. As noted above, each assay strip has an assay region 98 with a test dot 100 and a control dot 102 for indicating the presence or absence of one of a plurality of analytes in a liquid sample placed in the liquid sample space of the interior chamber of the container. As in the first embodiment, five assay strips are preferably provided, as is shown in FIG. 7. A container cup may optionally be provided, either connected to the test strip holder, or separately, for retaining excess or overflow sample. The sample tube may also optionally include a wick of a fibrous material that can be natural or synthetic, such as cotton, for conducting the liquid sample from the sample tube to the assay regions of each assay strip.

Figure 8:
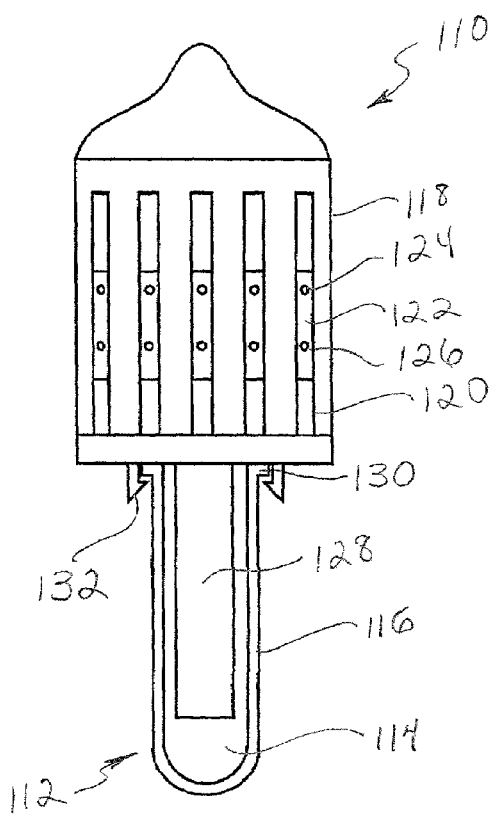
FIG. 8 is a schematic diagram of a fourth embodiment of the drug test kit according to the principles of the invention.

A fourth presently preferred embodiment is illustrated in FIG. 8, showing an assaying apparatus 110 including a sample container 112, such as a collection vial having an interior sample chamber 114 providing a liquid sample space for receiving a liquid sample, and an outer wall 116 serving as a protective shield, allowing the sample container to be used as a mailing tube. A test strip holder 118 is provided, adapted to mate with the sample container, and including one or more assay strips 120, as described above, disposed in the test strip holder, with each assay strip having an assay region 122 with a test dot 124 and a control dot 126 for indicating the presence or absence of one of a plurality of analytes in a liquid sample placed in the liquid sample space of the interior chamber of the container. A main wick 128, typically formed of a fibrous material that can be natural or synthetic, such as cotton, for example, is centrally mounted to the test strip holder, such as by adhesive, and is adapted to be inserted into the sample container when the test strip holder is placed on the container, for conducting the sample to the test strips. The wick is preferably an annular wick material, such as cotton, or other suitable natural or synthetic fabric, for example, for conducting a portion of the liquid sample from the sample container to the assay region of each assay strip. The sample container may advantageously have a lip 130 around the mouth of the sample container, adapted to be received by and retained by hooks 132 on the test strip holder, so that the sample container can be snapped onto the test strip holder.

Figure 9:
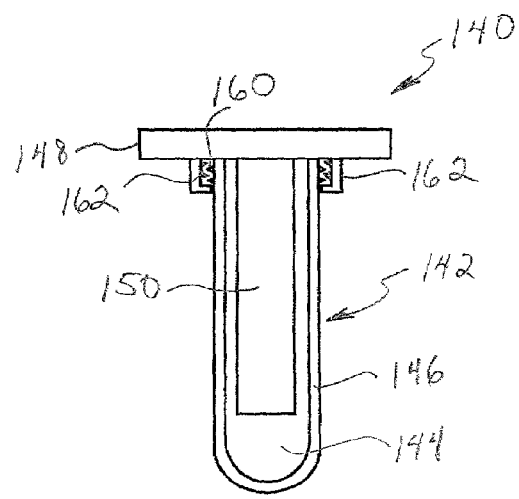
FIG. 9 is a side view of a fifth embodiment of the drug test kit according to the principles of the invention.
Figure 10:
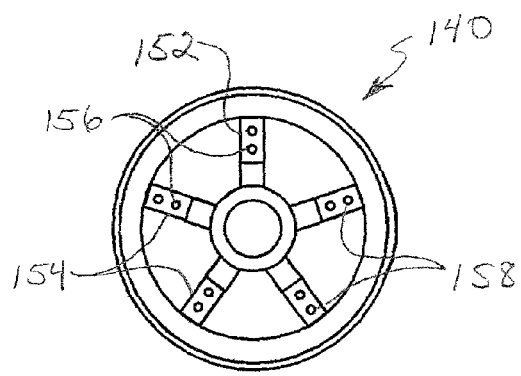
FIG. 10 is a top plan view of the drug test kit of FIG. 9.

In a fifth presently preferred embodiment, illustrated in FIGS. 9 and 10, an assaying apparatus 140 includes a sample container 142, such as a collection vial having an interior sample chamber 144 providing a liquid sample space for receiving a liquid sample, and an outer wall 146 serving as a protective shield, allowing the sample container to be used as a mailing tube. A test strip holder 148 is provided, adapted to mate with the sample container, and includes a main wick 150, for conducting liquid sample to one or more test strips 152 typically formed of a fibrous material that can be natural or synthetic, such as cotton, for example, that is centrally mounted to the test strip holder, such as by adhesive, and that is adapted to be inserted into the sample container when the test strip holder is placed on the container. The wick is adapted to be connected in fluid communication with the inner ends of one or more assay strips as described above, disposed in the test strip holder. As noted above, each assay strip has an assay region 154 with a test dot 156 and a control dot 158 for indicating the presence or absence of one of a plurality of analytes in a liquid sample placed in the liquid sample space of the interior chamber of the container. As in the second embodiment, five assay strips are preferably provided, as is shown in FIG. 10. The sample container may advantageously have threading 160 around the mouth of the sample container, adapted to be received by and retained by corresponding centrally located internal threading 162 on the test strip holder, so that the sample container can be connected to the test strip holder.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. Assaying apparatus for collecting and analyzing a liquid sample for an analyte in the liquid sample, the apparatus comprising:
   a container having an interior sample chamber with a liquid sample space, said container having a surface defining an opening in communication with said interior sample chamber;
   a cap adapted to be placed on said container opening for closing said container opening and sealing said container;
   an assay strip disposed in said cap, said assay strip having an assay region disposed in said cap for indicating the presence or absence of an analyte in a liquid sample placed in said liquid sample space of said interior chamber, and said cap including a separator member disposed between said assay strip and said interior sample chamber for separating said liquid sample space from said assay region of said assay strip;
   a wick mounted to said cap and extending into said liquid sample space of said interior sample chamber when said cap is placed on said container, said wick being in fluid communication with said assay strip for conducting a portion of the liquid sample from said interior chamber to said assay region of said assay strip; and
   an annular bridging wick piece connected between said wick and said assay strip in fluid communication with said wick and said assay strip and in immediate contact with said assay strip for conducting the liquid sample from said wick to said assay strip.

2. The assaying apparatus of claim 1, further comprising a transparent cover over said assay strip permitting observation of the results of the assay.

3. The assaying apparatus of claim 1, wherein said assay strip comprises wicking material for conducting the liquid sample from said wick to said assay region of said assay strip.

4. Assaying apparatus for collecting and analyzing a liquid sample for the presence or absence of a plurality of analytes in the liquid sample, the apparatus comprising:
   a container having an interior sample chamber with a liquid sample space, said container having a surface defining an opening in communication with said interior sample chamber;
   a cap adapted to be placed on said container opening for closing said container opening and sealing said container;
   a plurality of assay strips disposed in said cap, each assay strip having an assay region disposed in said cap for indicating the presence or absence of one of a plurality of analytes in a liquid sample placed in said liquid sample space of said interior chamber, and said cap including a separator member disposed between said assay strips and said interior sample chamber for separating said liquid sample space from said assay region of said assay strip;
   a wick mounted to said cap and extending into said liquid sample space of said interior sample chamber when said cap is placed on said container, said wick being in fluid communication with said assay strip for conducting a portion of the liquid sample from said interior chamber to said assay region of said assay strip; and
   an annular bridging wick piece connected between said wick and said assay strips in fluid communication with said wick and said assay strips and in immediate contact with said assay strips for conducting the liquid sample from said wick to said assay strips.

5. The assaying apparatus of claim 4, further comprising a transparent cover over said assay strips permitting observation of the results of the assays.

6. The assaying apparatus of claim 4, wherein said assay strips comprise wicking material for conducting the liquid sample from said wick to said assay regions of said assay strips.

* * * * *